(12) United States Patent
Chang

(10) Patent No.: US 11,224,332 B2
(45) Date of Patent: Jan. 18, 2022

(54) ENDOSCOPE WITH CAMERA MODULE TURNING FUNCTION

(71) Applicants: IEI INTEGRATION CORP., New Taipei (TW); ARMORLINE SH CORP., Shanghai (CN)

(72) Inventor: Chin-Chia Chang, New Taipei (TW)

(73) Assignees: IEI INTEGRATION CORP., New Taipei (TW); ARMORLINK SH CORP., Shanghai (CN)

( * ) Notice: Subject to any disclaimer, the term of this patent is extended or adjusted under 35 U.S.C. 154(b) by 243 days.

(21) Appl. No.: 16/424,717

(22) Filed: May 29, 2019

(65) Prior Publication Data

US 2020/0268235 A1 Aug. 27, 2020

(30) Foreign Application Priority Data

Feb. 25, 2019 (CN) .......................... 201910137754.4

(51) Int. Cl.
| | |
|---|---|
| *A61B 1/00* | (2006.01) |
| *A61B 1/005* | (2006.01) |
| *A61B 1/05* | (2006.01) |
| *A61B 17/00* | (2006.01) |

(52) U.S. Cl.
CPC ........ *A61B 1/00181* (2013.01); *A61B 1/0051* (2013.01); *A61B 1/0057* (2013.01); *A61B 1/00096* (2013.01); *A61B 1/05* (2013.01); *A61B 1/00009* (2013.01); *A61B 1/0011* (2013.01); *A61B 1/00105* (2013.01); *A61B 1/00188* (2013.01); *A61B 2017/00318* (2013.01)

(58) Field of Classification Search
USPC ................................................. 600/147, 149
See application file for complete search history.

(56) References Cited

U.S. PATENT DOCUMENTS

| | | | | |
|---|---|---|---|---|
| 3,897,775 | A * | 8/1975 | Furihata | ................. A61B 1/015 600/131 |
| 4,483,326 | A * | 11/1984 | Yamaka | ............... A61B 1/0057 600/141 |
| 5,944,690 | A * | 8/1999 | Falwell | ............. A61M 25/0136 604/170.03 |
| 6,648,875 | B2 * | 11/2003 | Simpson | ........... A61M 25/0136 600/585 |
| 9,314,593 | B2 * | 4/2016 | Schaeffer | ............... A61B 1/233 |
| 9,901,370 | B2 * | 2/2018 | Kim | .................. A61B 17/3478 |

(Continued)

*Primary Examiner* — John P Leubecker

(57) ABSTRACT

An endoscope with a camera module turning function is revealed. The endoscope includes a housing provided with a mounting slot and an output portion, an insertion tube connected to the output portion, a bending member connected to the insertion tube and having a first upper turning hole and a lower turning hole, a first upper string passed through the first upper turning hole of the bending member and mounted in the insertion tube, a lower string passed through the lower turning hole of the bending member and disposed in the insertion tube, a first roller provided with a first string groove on the circumference thereof, a control member provided with a pin and a connecting rod, and an elastic member fixed on the housing and connected to the lower string. The pin is connected to the first roller while the connecting rod is connected to the pin and a control button.

11 Claims, 17 Drawing Sheets

(56) References Cited

U.S. PATENT DOCUMENTS

| | | | |
|---|---|---|---|
| 2007/0232858 A1* | 10/2007 | Macnamara | A61B 1/0052 600/149 |
| 2011/0082337 A1* | 4/2011 | Boulais | A61B 1/0052 600/146 |
| 2018/0207401 A1* | 7/2018 | Wang | A61M 16/0472 |

* cited by examiner

ENDOSCOPE WITH CAMERA MODULE TURNING FUNCTION

BACKGROUND OF THE INVENTION

Field of the Invention

The present invention relates to an endoscope, especially to an endoscope with a camera module turning function.

In modern medical tests, certain procedures such as gastroscopy, colonoscopy, etc. should be performed by apparatuses such as endoscope because human eyes cannot see organs inside the body. The endoscope is one of essential devices used for medical test. With the assistance of the endoscope, medical personnel can find out lesions and symptoms for diagnosis of various diseases.

Generally, the endoscope available now includes a handle with one end thereof connected to a long, thin catheter inserted into human bodies. A distal end of the catheter is connected to a camera module for capturing images inside the human body. Then the images captured are transmitted to a screen connected to the other end of the catheter by wires embedded in the catheter or a wireless transmission part so that medical staff can observe and treat patients directly. In order to make the endoscope enter curved passages smoothly and get images at different angles and positions inside human body, a flexible tube is arranged at a distal end of the catheter for control of swing of the catheter and further turning of the camera module in the front end thereof. Thus the endoscope can insert deep into the curved passages smoothly to get multi-angle images inside the body.

The most common bending member available is formed by a plurality of units having the same shape is mounted in the flexible tube on the distal end of the catheter. The two adjacent units are pivotally connected by rivets so that they can swing to change the angle therebetween. A plurality of units is connected in turn to form a turning control assembly that is mounted in the flexible tube on the distal end of the catheter. In combination with a string inserted through preset holes on each of two sides of the respective unit, the flexible tube can be curved. The shooting angle of the camera module at the distal end is further controlled to obtain images at different positions inside the body.

However, the medical staff member controls 3-dimensional swing by an operating rod together with the direction of the wrist movement. Cavities inside the body are 3-dimensional space so that medical personnel may lose the direction of the target while controlling/adjusting bending angle of the flexible tube inside the cavity of the body. The control of the turning is more complicated.

Thus there is room for improvement and there is a need to provide an endoscope with novel design that solves the problems of direction loss occurred while controlling/adjusting bending angle of the flexible tube inside the cavities of the body and complexity in turn control.

SUMMARY OF THE INVENTION

Therefore it is a primary object of the present invention to provide an endoscope with a camera module turning function that allows medical staff to turn a camera module of the endoscope toward one specific direction and improves the operating convenience of the endoscope.

It is another object of the present invention to provide an endoscope with a camera module turning function that allows doctors to control turning of the camera module only toward one direction by an automatic spring-back turning mechanism composed of an elastic member connected to a lower string. Thus the endoscope is more convenient to operate.

It is a further object of the present invention to provide an endoscope with a camera module turning function in which the position and the angle of a camera module of the endoscope can be fixed or adjusted slightly by a position control member for allowing medical personnel to examine patients carefully.

It is a further object of the present invention to provide an endoscope with a camera module turning function in which a first stop hole of a stop member is aligned with an output tube for allowing users to make a bending member bend by pulling a first upper string with less effort and improving convenience in use.

It is a further object of the present invention to provide an endoscope with a camera module turning function that allows users to make a bending member bend by pulling a first upper string and a second upper string stably with less effort. Thus not only the endoscope is more convenient to use, the chance of breaking strings is also reduced and the service life of the product is further increased.

In order to achieve the above objects, an endoscope with a camera module turning function according to the present invention includes a housing, an insertion tube, a bending member, a first upper string, a lower string, a first roller, a control member and an elastic member. The housing consists of a mounting slot and an output portion. The mounting slot is located on an upper end thereof and provided with a first insertion hole while the output portion has an output tube which is hollow and located on the front end of the housing. The insertion tube is hollow and one end thereof is connected to the output portion. One end of the bending member is connected to the other end of the insertion tube and the other end thereof is provided with a camera module. Two symmetrical tube walls of the bending member are provided with a first upper turning hole and a lower turning hole, respectively. The first upper string is passed through the first upper turning hole on one of the two tube walls of the bending member and mounted in the insertion tube while the lower string is arranged symmetrically to the first upper string, passed through the lower turning hole on the other tube wall of the bending member and disposed in the insertion tube. The first roller is provided with a first string groove on the circumference thereof and one end of the first upper string is connected to the first string groove. The control member is composed of a pin, a connecting rod and a control button. One end of the pin is inserted through the first insertion hole of the mounting slot and connected to the center of the first roller while one end of the connecting rod is connected to the pin and the other end of the connecting rod is connected to the control button. The pin is perpendicular to the connecting rod. As to the elastic member, one end thereof is fixed on the housing and the other end thereof is connected to the lower string.

The endoscope with a camera module turning function of the present invention further includes a stop member fixed on the housing. The stop member is provided with a first stop hole that is aligned with the output tube. The first upper string is passed through the first stop hole and the output tube to be connected to the bending member.

The endoscope with a camera module turning function of the present invention further includes a position control member that is composed of a positioning operating part, a connecting part, an elastic part and a zigzag fixing part. One end of the connecting part is connected to the positioning operating part while the other end of the connecting part is inserted through a positioning hole of the housing and connected to the zigzag fixing part. The elastic part is inserted by the connecting part and locked between the housing and the zigzag fixing part. A plurality of saw teeth is disposed on the circumference of the inner side of the first roller while a lower part of the zigzag fixing part is jagged and able to engage with one of the saw teeth of the first roller.

In order to achieve the above objects, an endoscope with a camera module turning function according to the present invention includes a housing, an insertion tube, a bending member, a first upper string, a second upper string, a lower string, a first roller, a second roller, a control member and an elastic member. The housing consists of a mounting slot and an output portion. The housing consists of a mounting slot and an output portion. The mounting slot is located on an upper end thereof and provided with a first insertion hole and a second insertion hole while the output portion has a hollow output tube located on the front end of the housing. The insertion tube is hollow and one end thereof is connected to the output portion. One end of the bending member is connected to the other end of the insertion tube and the other end thereof is provided with a camera module. An upper tube wall of the bending member is provided with a first upper turning hole and a second upper turning hole while a lower tube wall of the bending member is provided with a lower turning hole. The lower turning hole is aligned within the area between the first upper turning hole and the second upper turning hole. The first upper string is passed through the first upper turning hole of the bending member and mounted in the insertion tube while the second string is passed through the second upper turning hole of the bending member and located in the insertion tube. As to the lower string, it is passed through the lower turning hole and disposed in the insertion tube. The first roller is provided with a first string groove on the circumference thereof and one end of the first upper string is connected to the first string groove. A second string groove is formed on the circumference of the second roller and one end of the second upper string is connected to the second string groove. The control member is composed of a pin, a connecting rod and a control button. Two ends of the pin are inserted through the first insertion hole and a second insertion hole of the mounting slot to be connected to the center of the first roller and the center of the second roller, respectively. One end of the connecting rod is perpendicular and connected to the pin and the other end of the connecting rod is connected to the control button. As to the elastic member, one end thereof is fixed on the housing and the other end thereof is connected to the lower string.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
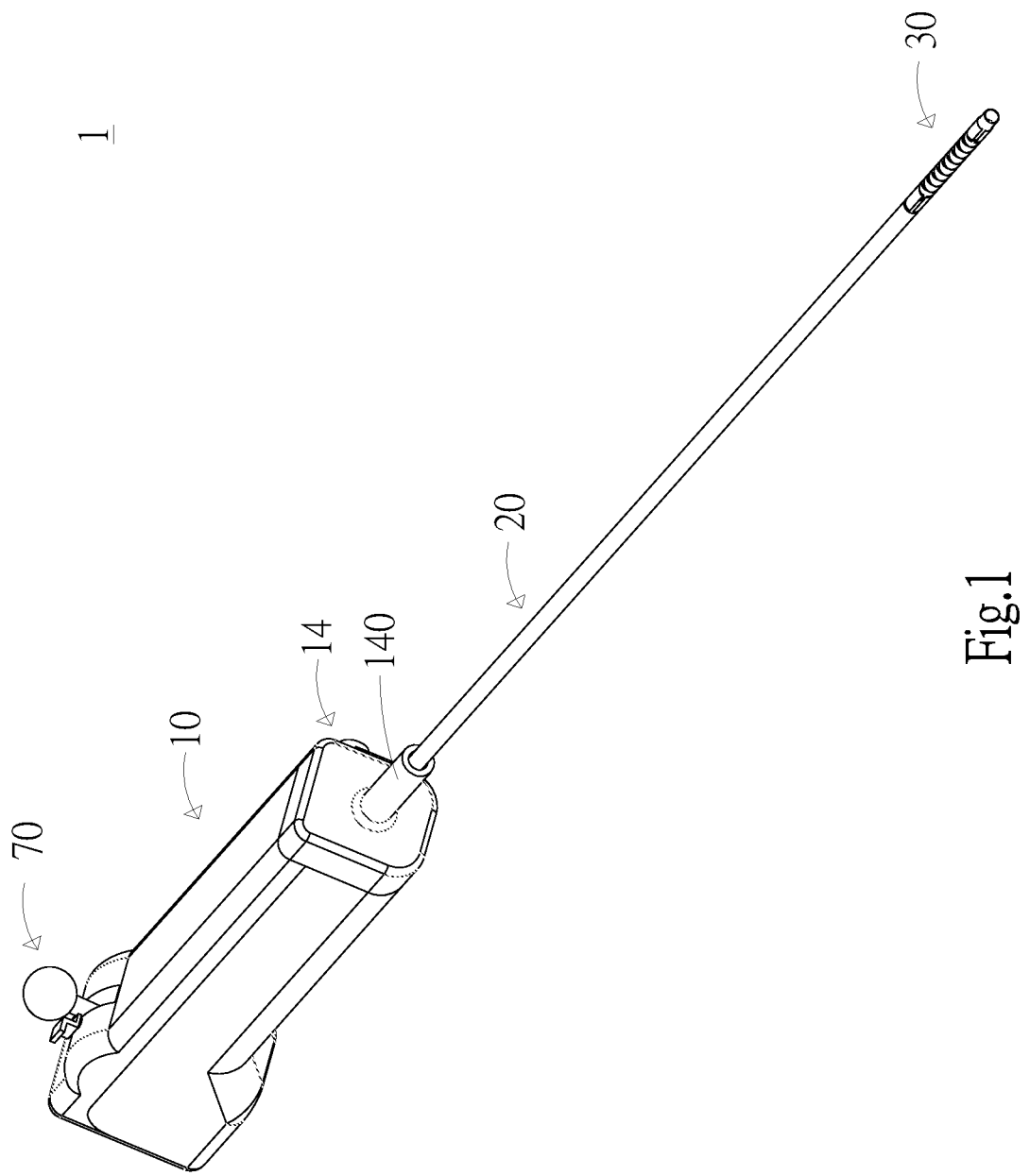
FIG. 1 is a perspective view of an embodiment according to the present invention.

Although the present invention herein has been described with reference to various exemplary embodiments, it is to be understood that these embodiments are merely illustrative of the principles and applications of the present invention. Those having skill in the art would recognize that various modifications to the exemplary embodiments may be made, without departing from the scope of the invention.

It is to be understood that the term "center", "longitudinal", "lateral", "length", "width", "upper", "lower", "front", "rear", "left", "right", "top", "bottom", "inner", "clockwise", "counterclockwise", or the like indicates directions or positions shown in the accompanying drawings, only used for convenience of description. The term does not indicate or imply that the device or element referred to must have a specific direction, or must be constructed and operated in a specific direction. Thus it is not intended to limit the present invention.

In addition, the terms "the first", "the second" are only used for description, not to indicate or imply relative importance or the amount of technical features. Thus, the features defined by "the first", "the second" may include one feature or more than one feature. Unless specifically stated, "a plurality of" means "at least two".

In the present invention, it should be noted that, unless explicitly specified or limited, the terms "mounted," "connected to", "connected", "fixed" should be interpreted in the broadest possible manner. For example, "connection" could refer to a fixed connection, a removable connection, an integral connection; a mechanical connection or an electrical connection; a direct connection, an indirect connection through a medium, or communication between interior of the two elements. Those of ordinary skill in the art would understand the meaning of the terms.

In the present invention, unless explicitly specified and defined, the first element is "on", "above", "over" the second element means the position of the first element is higher than the position of the second element. The first element and the second element have direct or indirect contact therebetween. The first element is "beneath", "below" and "under" the second element means that the first element is at a higher position than the second element. The first element and the second element have direct or indirect contact therebetween.

Although certain terms in the embodiments and the claims are used to represent particular components, it is to be understood that hardware manufacturers may use different terms to refer to the same component. The components in the embodiments and the claims can be distinguished by their difference in function, instead of difference in term. As used herein, the terms "comprising", "comprises", "include", "includes", "including" and "having" are meant to be non-limiting.

Refer to FIG. 1, FIG. 2, FIG. 3 and FIG. 4, an endoscope with a rotatable camera module 1 according to the present invention includes a housing 10, an insertion tube 20, a bending member 30, a first upper string 40, a lower string 50, a first roller 60, a control member 70 and an elastic member 80. The housing 10 consists of a mounting slot 12 with a first insertion hole 120 and an output portion 14. The mounting slot 12 is located on a surface of an upper end of the housing 10. In this embodiment, the mounting slot 12 is, but not limited to, a rectangular slot and used for mounting the control member 70 therein.

The housing 10 further includes an upper housing 100 and a lower housing 102. The mounting slot 12 is disposed on the upper housing 100. After the upper and lower housings 100, 102 being assembled, the output portion 14 is arranged at the front end of the assembly of the upper housing 100 and the lower housing 102. The output portion 14 is provided with an output tube 140 which is hollow and located on the front end of the housing 10.

Figure 3:
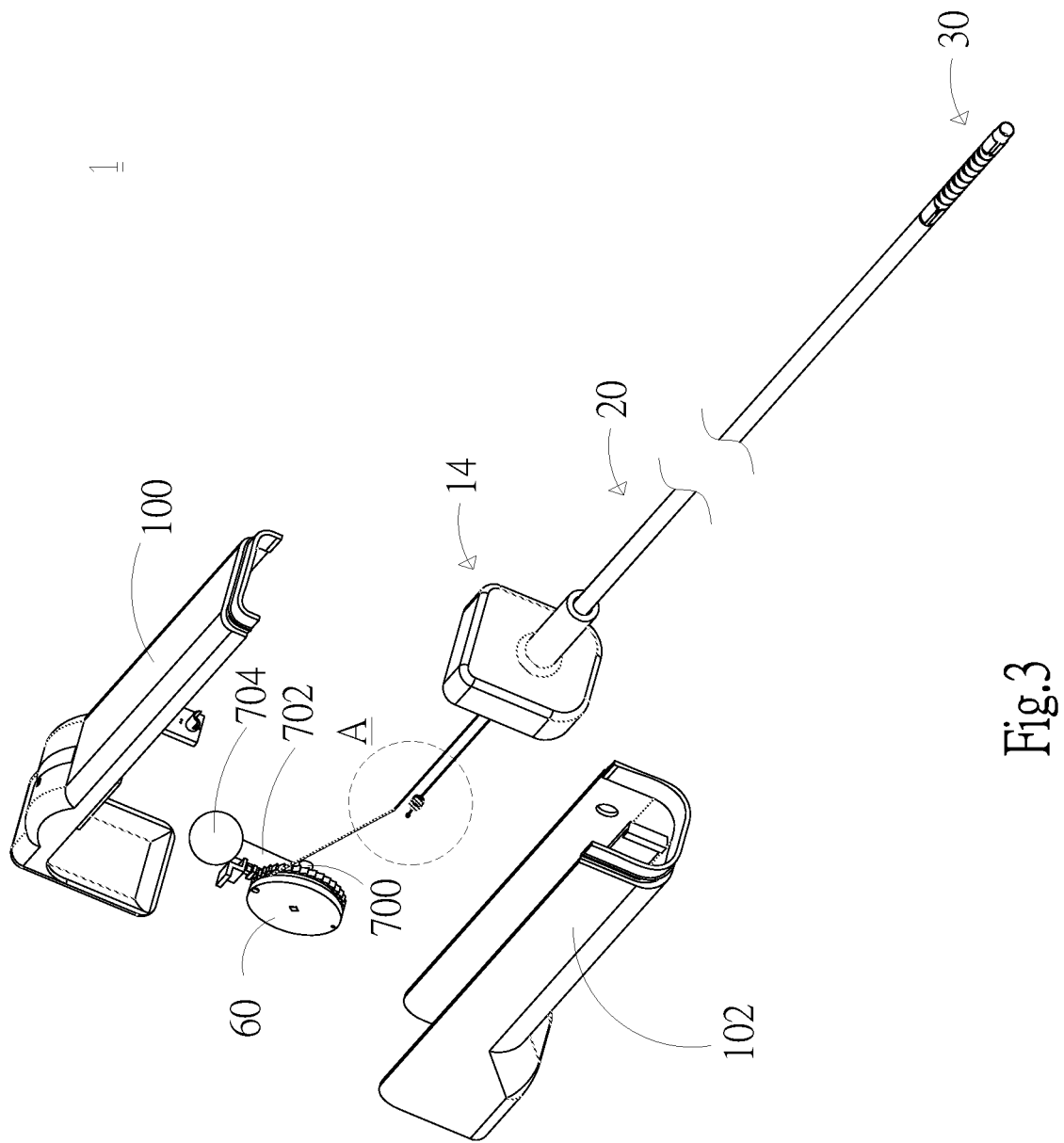
FIG. 3 is an explosive view of an embodiment according to the present invention.
Figure 5:
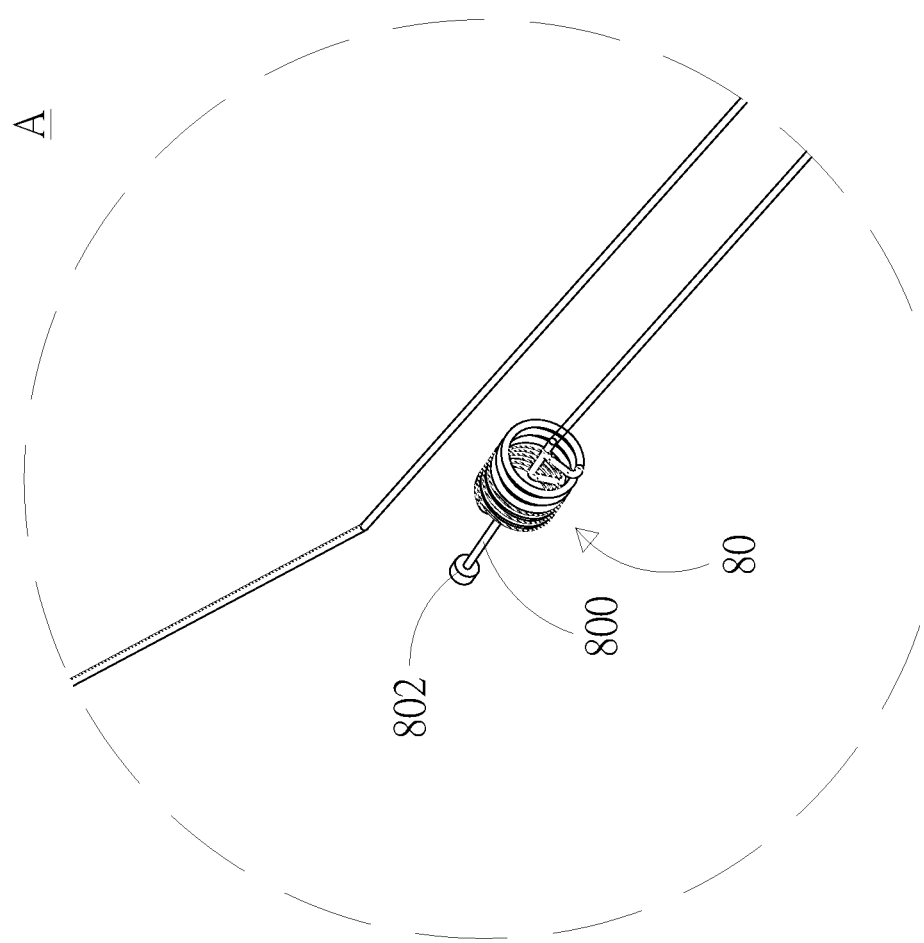
FIG. 5 is an enlarged view of the part A of the embodiment in FIG. 3 according to the present invention.
Figure 9:
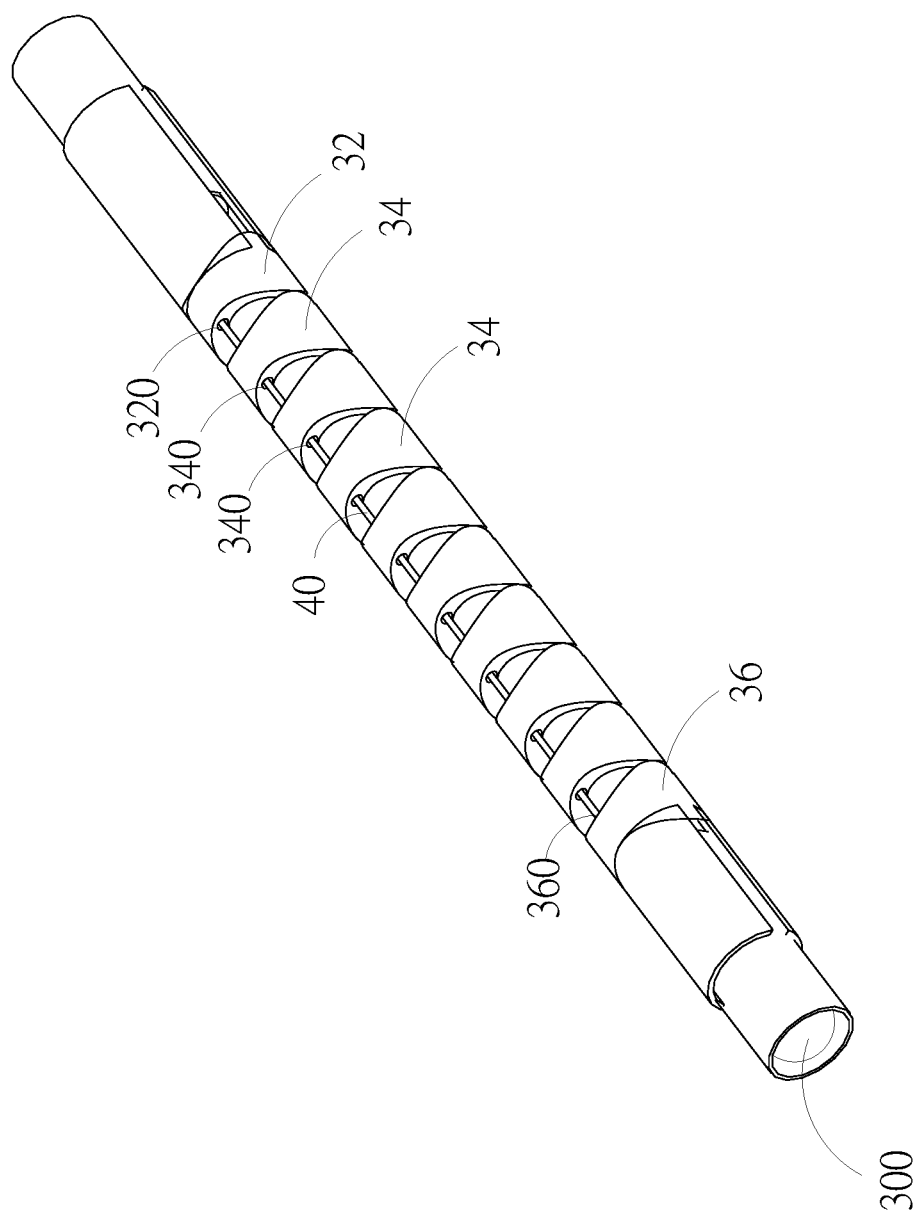
FIG. 9 is a schematic drawing showing a bending member of an embodiment according to the present invention.
Figure 10:
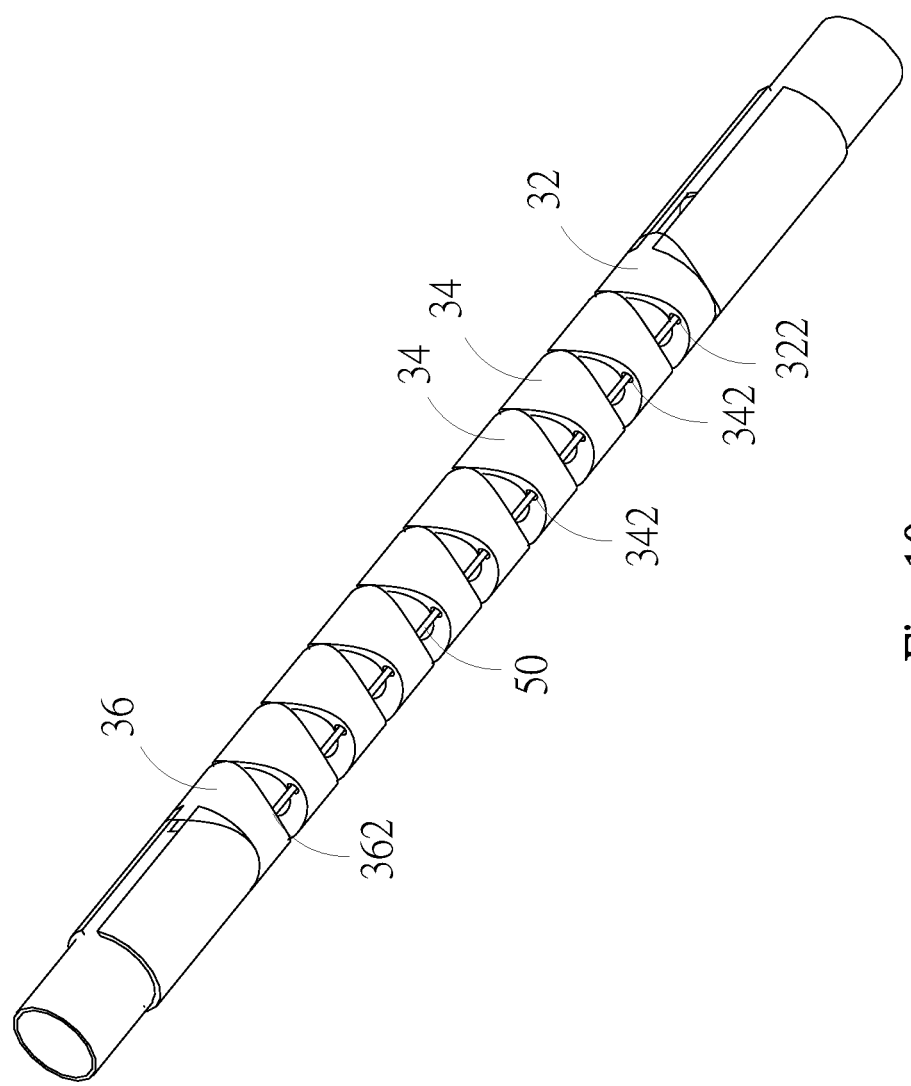
FIG. 10 is another schematic drawing showing a bending member of an embodiment according to the present invention.
Figure 13:
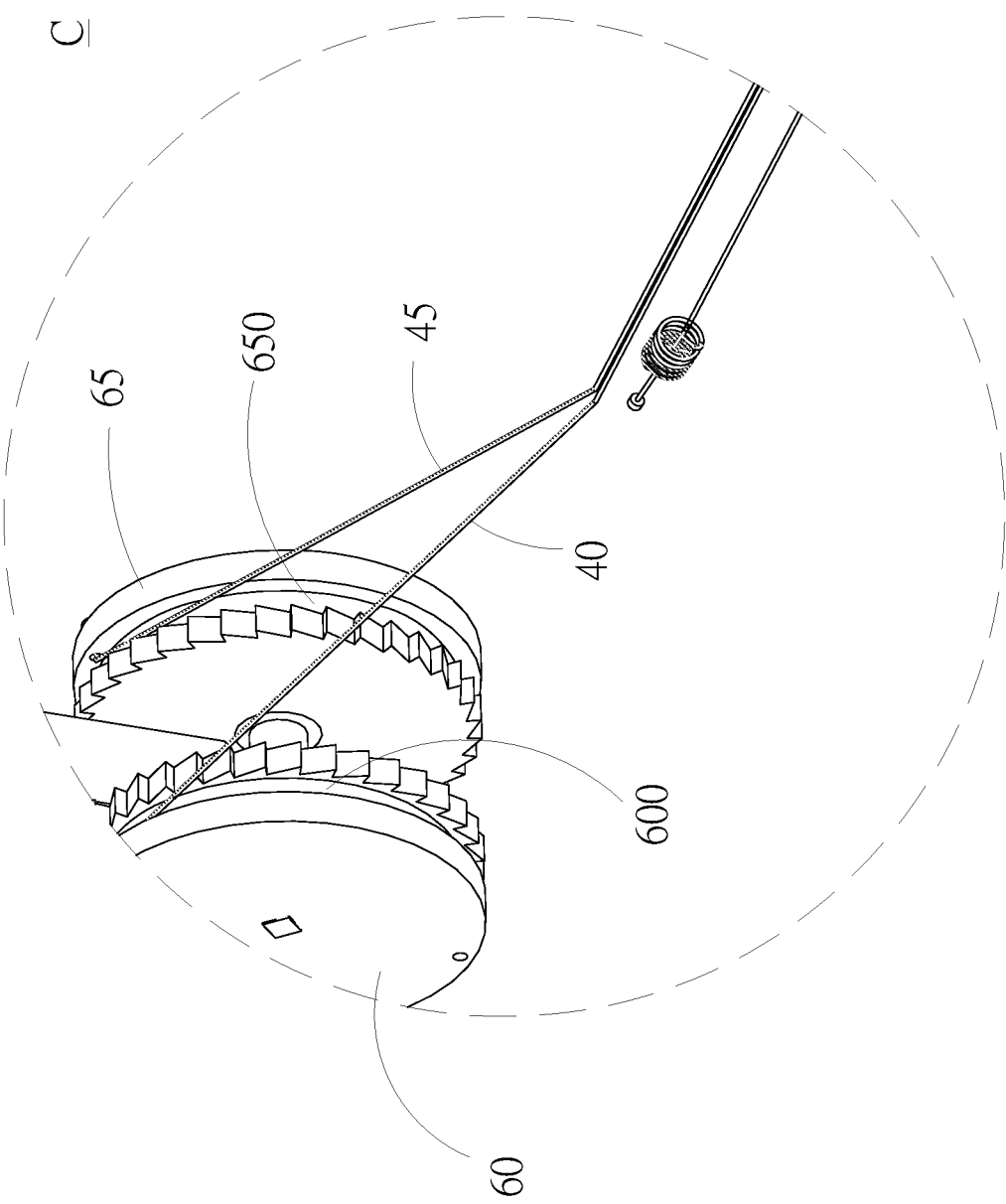
FIG. 13 is an enlarged view of the part C of the embodiment in FIG. 11 according to the present invention.

The insertion tube 20 is a hollow tube having one end thereof connected to the output portion 14 and the other end thereof connected to one end of the bending member 30. The other end of the bending member 30 is provided with a camera module 300 (as shown in FIG. 9). Two symmetrical tube walls of the bending member 30 are provided with a first upper turning hole (a collective term given to a first front upper turning hole 320, a first middle upper turning hole 340, and a first rear upper turning hole 360, as shown in FIG. 9) and a lower turning hole (a collective term for a front lower turning hole 322, a middle lower turning hole 342, and a rear lower turning hole 362, as shown in FIG. 10), respectively. The first upper string 40 is passed through the first upper turning hole 320, 340, 460 on one of the two tube walls of the bending member 30 and mounted in the insertion tube 20 while the lower string 50 is arranged symmetrically to the first upper string 40, passed through the lower turning holes 322, 342, 362 on the other tube wall of the bending member 30 and disposed in the insertion tube 20. As shown in FIG. 13, a first string groove 600 is formed on the circumference of the first roller 60 and one end of the first upper string 40 is connected to the first string groove 600. Refer to FIG. 3, the control member 70 is composed of a pin 700, a connecting rod 702 and a control button 704. One end of the pin 700 is inserted through the first insertion hole 120 of the mounting slot 12 and connected to the center of the first roller 60 while one end of the connecting rod 702 is connected to the pin 700 and the other end of the connecting rod 702 is connected to the control button 704. The pin 700 and the connecting rod 702 are perpendicular to each other. Refer to FIG. 3 and FIG. 5, one end of the elastic member 80 is fixed on the housing 10 while the other end thereof is connected to the lower string 50.

Users operate the control button 704 of the control member 70 to cause the bending member 30 to be bent upward or downward. More specifically, the first upper string 40 is pulled and released by the manual operation of the control button 704. When the user operates the control button 704 to pull the first upper string 40, the bending member 30 is bent and moved upward. Once the first upper string 40 is pulled to the limit by operating the control button 704, the bending member 30 has been bent upward completely. When the user stops operating the control button 704, the elastic member 80 starts compression to pull the lower string 50 to cause the bending member 30 to move downward because the lower string 50 is located on the lower part of the bending member 30 and one end of the lower string 50 is connected to the elastic member 80. When the elastic member 80 is compressed to the maximum, the bending member 30 has been bent downward completely. Thereby the present invention allows doctors to turn the camera module of the endoscope 1 toward only one direction by an automatic spring-back turning mechanism composed of the elastic member 80 connected to the lower string 50. The purpose of convenient operation is achieved.

Figure 6A:
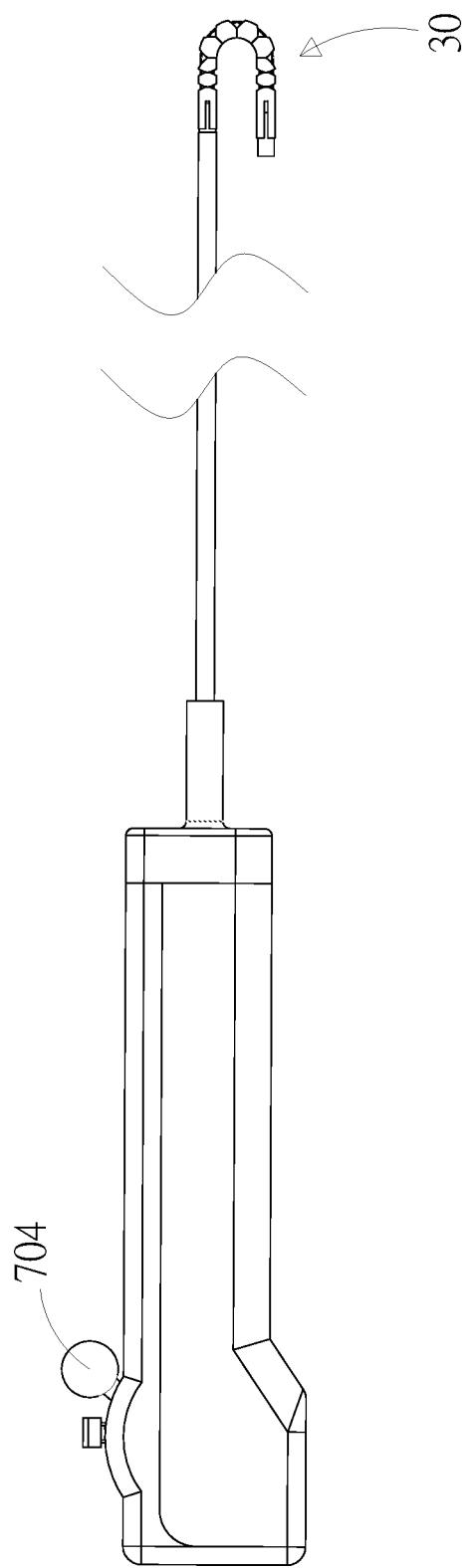
FIG. 6A is a schematic drawing showing action of an embodiment according to the present invention.
Figure 6B:
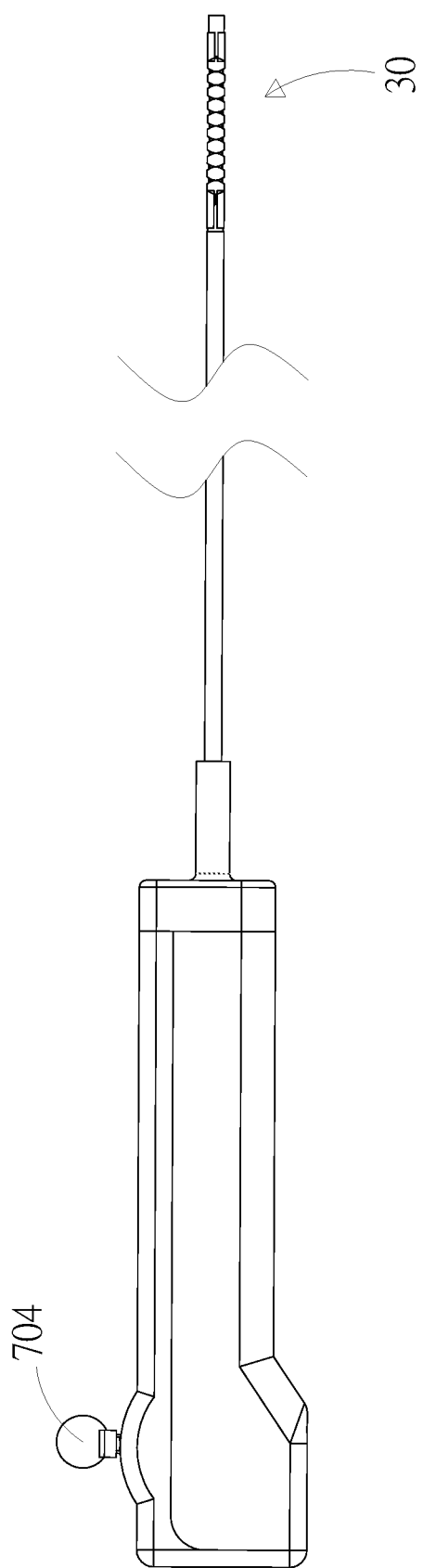
FIG. 6B is another schematic drawing showing action of an embodiment according to the present invention.
Figure 6C:
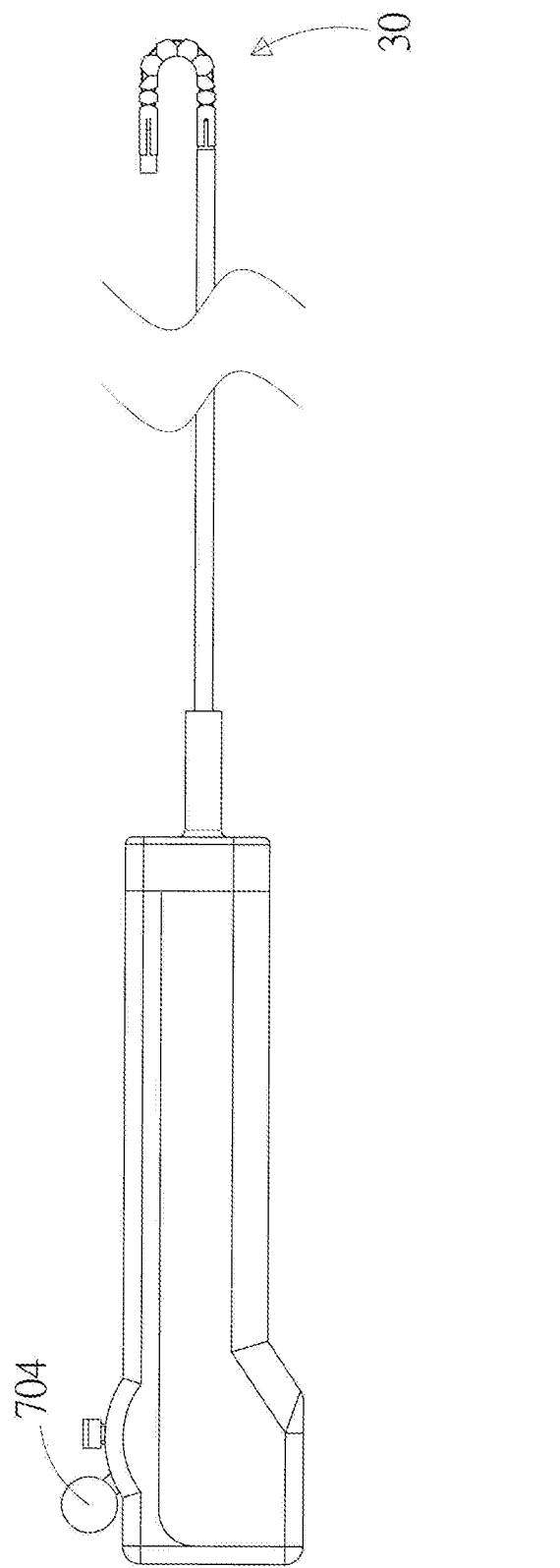
FIG. 6C is a further schematic drawing showing action of an embodiment according to the present invention.

In order to learn action of the present invention, refer to FIG. 6A, FIG. 6B, and FIG. 6C. As shown in FIG. 6A, the control button 704 is located at the front-most position and the elastic member 80 is completely compressed so that the lower string 50 is in the completely-tight state (the lower string 50 is pulled to the limit) when the endoscope is not in use. Yet the first upper string 40 is in the completely-released state. Thereby the bending member 30 is bent downward now.

Refer to FIG. 6B, when the user operates the control button 704 to move the control button 704 to the middle position, both the first upper string 40 and the lower string 50 are pulled to about a half of the maximum movement. Thus the bending member 30 is straight, with no bends or kinks.

Refer to FIG. 6C, when the user operates the control button 704 to move the control button 704 to the rear-end position, the first upper string 40 is in the completely-tight state and the lower string 50 is in the completely-released state while the elastic member 80 is completely extended. Thus the bending member 30 is bent upward.

As shown in FIG. 6A, FIG. 6B and FIG. 6C, it is learned that doctors can turn the endoscope 1 toward only one direction by an automatic spring-back turning mechanism composed of the elastic member 80 connected to the lower string 50. The purpose of convenient operation is achieved.

Figure 2:
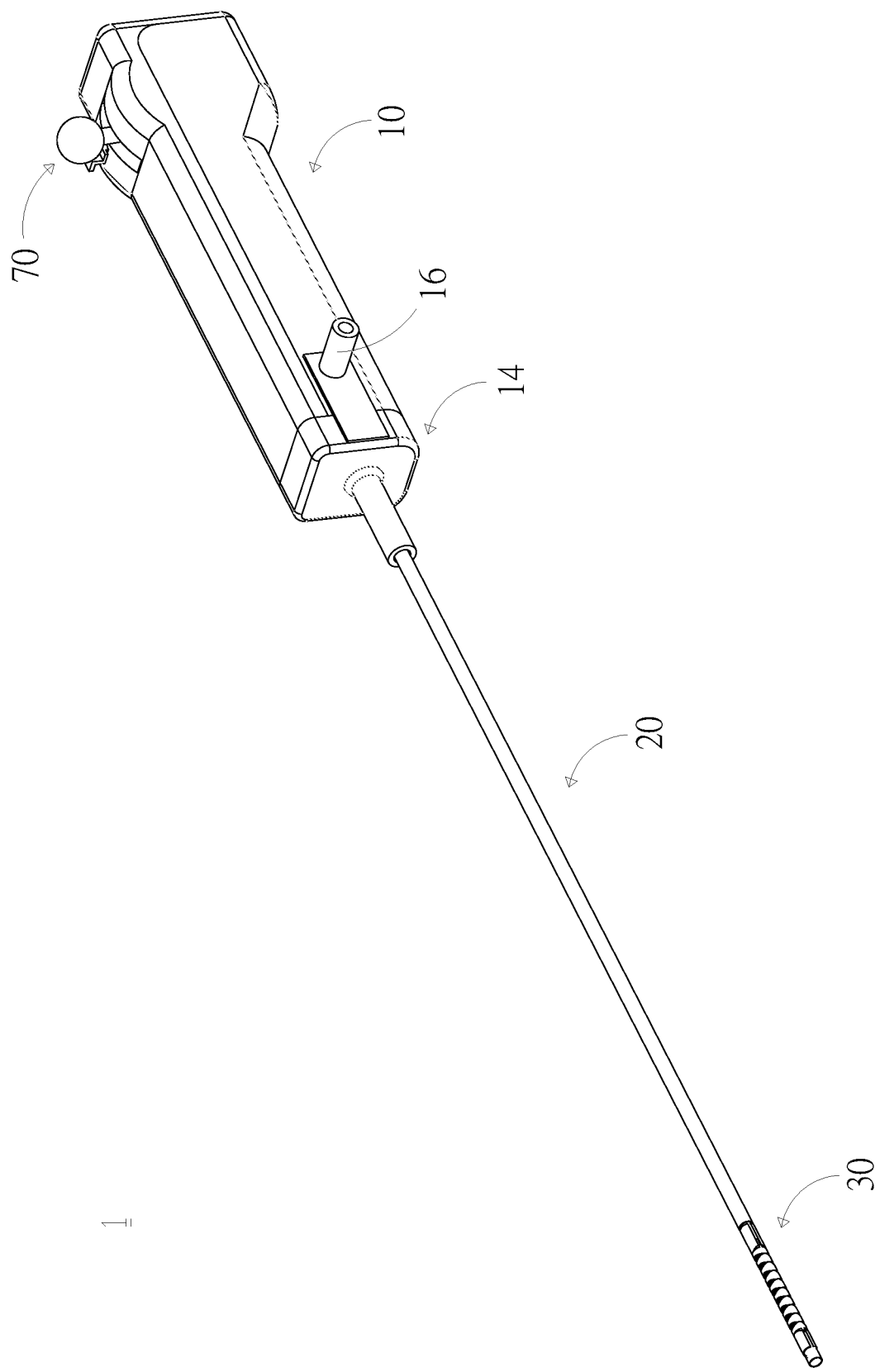
FIG. 2 is a perspective view of an embodiment from another angle according to the present invention.

Moreover, as shown in FIG. 2, the present endoscope 1 further includes a communication tube 16 that is connected to one side of the housing 10 and used for connecting to screens or computers to read image captured by the camera module 300.

Figure 4:
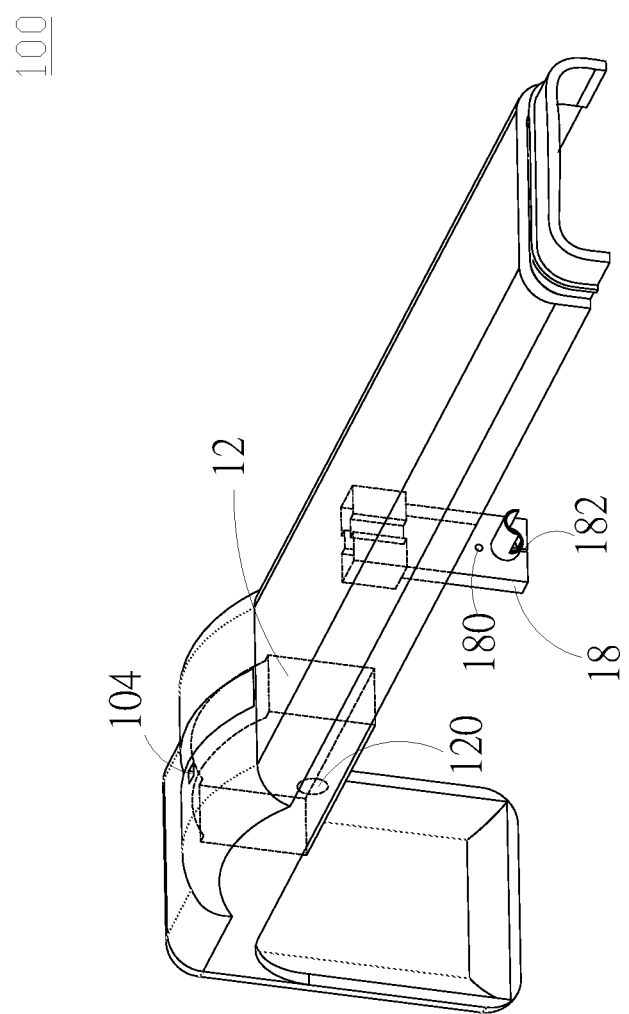
FIG. 4 is a schematic drawing showing a partial perspective view of an upper housing of an embodiment according to the present invention.
Figure 7:
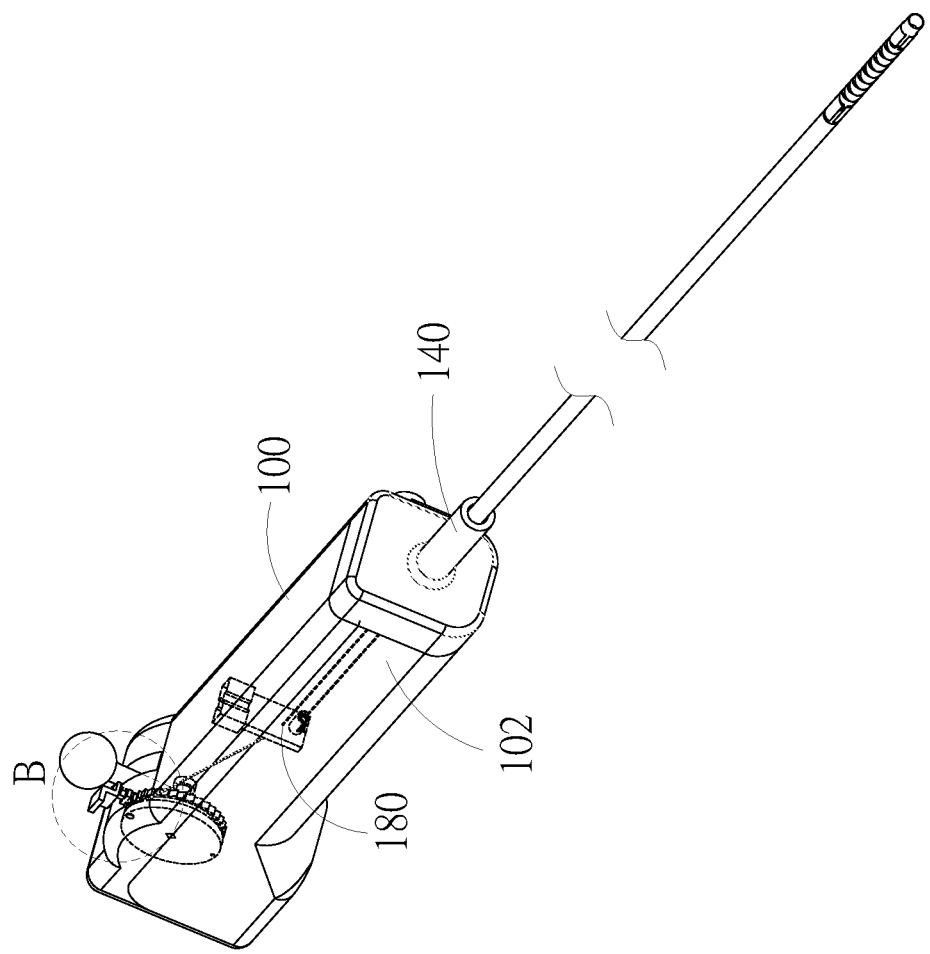
FIG. 7 is a schematic drawing showing a partial perspective view of an embodiment according to the present invention.

Refer to FIG. 4, FIG. 5, and FIG. 7. FIG. 5 is an enlarged view of the part A of the embodiment of the FIG. 3. FIG. 7 is a schematic drawing showing a partial perspective view. An endoscope 1 with a camera module turning function according to the present invention further includes a stop member 18 that is fixed on the housing 10. In this embodiment, the stop member 18 is arranged at the upper housing 100. The position of the stop member 18 is not restricted and the stop member 18 can also be disposed on the lower housing 100 as long as the stop member 18 is set on the housing 10. The stop member 18 consists of a first stop hole 180 and a fixing gap 182. The first stop hole 180 is aligned with the center of the output tube 140 so that the first upper string 40 is passed through the first stop hole 180 and the output tube 140 to be connected to the bending member 30. By the first stop hole 180 of the stop member 18 being aligned with the center of the output tube 140, users can pull the first upper string 40 easily to cause the bending member 30 to bend with less effort and the endoscope 1 is more convenient to use.

Furthermore, one end of the elastic member 80 is provided with a fixing bar 800 and a fixing piece 802. One end of the fixing bar 800 is connected to the elastic member 80 while the other end thereof is inserted through the fixing gap 182 and connected to the fixing piece 802 for fixing the elastic member 80 on the stop member 18. The elastic member 80 is not limited to be disposed on the stop member 18 as long as the elastic member 80 is disposed on the housing 10. For example, a fixing plate is arranged at the lower housing 102 and then the elastic member 80 is disposed on the fixing plate.

Figure 8:
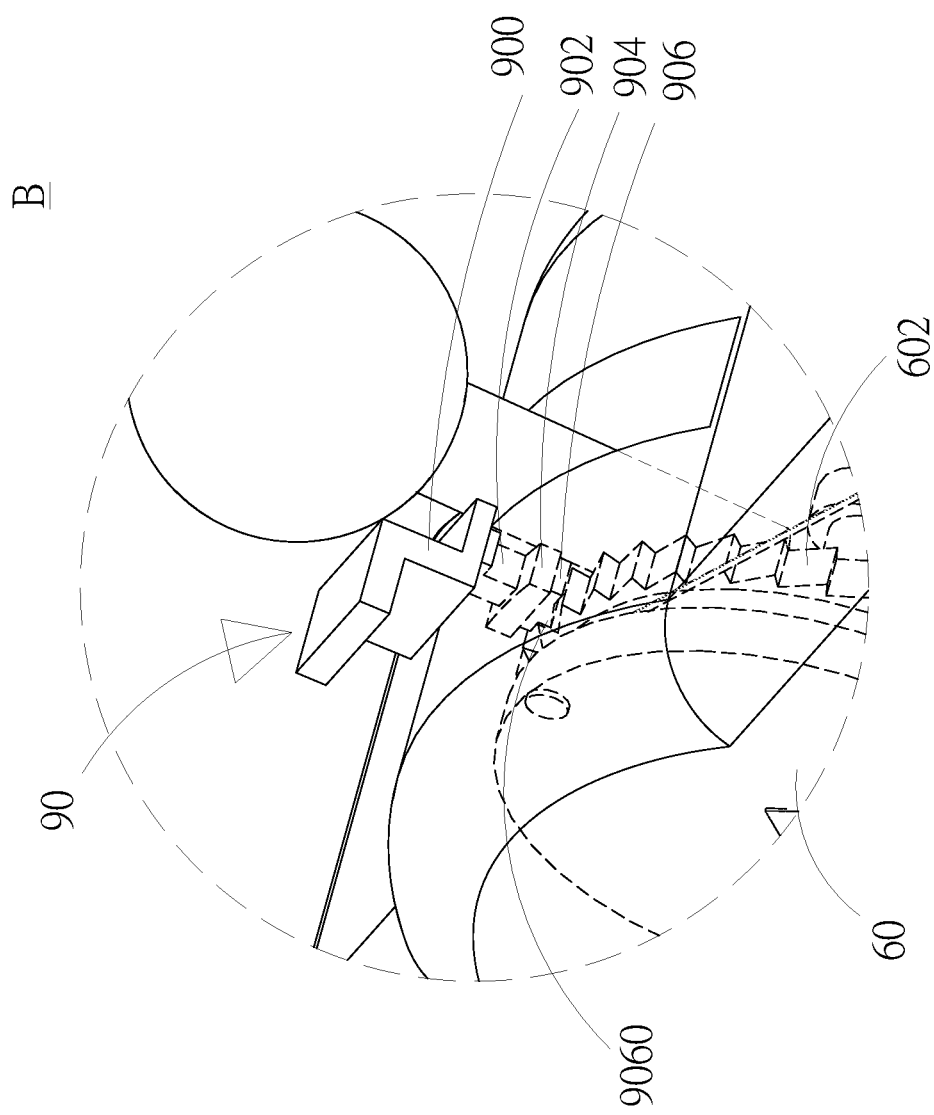
FIG. 8 is an enlarged view of the part B of the embodiment in FIG. 7 according to the present invention.

Refer to FIG. 8, an endoscope with a rotatable camera module 1 according to the present invention further includes a position control member 90 that is composed of a positioning operating part 900, a connecting part 902, an elastic part 904 and a zigzag fixing part 906. One end of the connecting part 902 is connected to the positioning operating part 900 while the other end of the connecting part 902 is inserted through a positioning hole 104 of the housing 10 (as shown in FIG. 4) and connected to the zigzag fixing part 906. The elastic part 904 is inserted by the connecting part 902 and locked between the housing 10 and the zigzag fixing part 906. The circumference of the inner side of the first roller 60 is provided with a plurality of saw teeth 602 while a lower part of the zigzag fixing part 906 is jagged and able to engage with the one of the saw teeth 602 of the first roller 60 for fixing. Thereby the position and the angle of the camera module of the endoscope can be fixed or adjusted slightly by the position control member 90 so that medical personnel can examine patients carefully.

Refer to FIG. 9 and FIG. 10, the bending member 30 is viewed from different angles. As shown in the figures, the bending member 30 includes a front turning tube 32, a plurality of turning tubes 34, a rear turning tube 36 and a camera module tube 38. One end of the front turning tube 32 is connected to the rear end of the insertion tube 20 while an upper tube wall and a lower tube wall of the front turning tube 32 are provided with a first front upper turning hole 320 and a front lower turning hole 322 respectively. The turning tubes 34 are arranged behind the front turning tube 32 in turn while an upper tube wall and a lower tube wall of each of the turning tubes 34 are provided with a first middle upper turning hole 340 and a middle lower turning hole 342 respectively. The first middle upper turning holes 340 of the turning tubes 34 are aligned and so are the middle lower turning holes 342. Moreover, the first middle upper turning hole 340 and the middle lower turning hole 342 of the turning tube 34 are aligned with the first front upper turning hole 320 and the front lower turning hole 322 respectively.

The rear turning tube 36 is disposed behind the turning tubes 34. An upper tube wall and a lower tube wall on one end of the rear turning tube 36 are provided with a first rear upper turning hole 360 and a rear lower turning hole 362 respectively. The first rear upper turning hole 360 and the rear lower turning hole 362 are aligned with the first middle upper turning holes 340 and the middle lower turning holes 342 of the turning tubes 34 respectively. The camera module tube 38 is connected to the other end of the rear turning tube 36. The first upper string 40 is passed through the first front upper turning hole 320, the first middle upper turning holes 340 and the first rear upper turning hole 360 to be fixed on the rear turning tube 36. The lower string 50 is passed through the front lower turning hole 322, the middle lower turning holes 342 and the rear lower turning hole 362 to be fixed on the rear turning tube 36. The first front upper turning hole 320, the first middle upper turning holes 340 and the first rear upper turning hole 360 are collectively called as the "first upper turning hole". Similarly, the front lower turning hole 322, the middle lower turning holes 342 and the rear lower turning hole 362 are collectively called as the "lower turning hole". Moreover, a V-shaped opening is formed between the two adjacent holes of the first upper turning hole 320, 340, 360 and an inverted V-shaped opening is formed between the two adjacent holes of the lower turning hole 322, 342, 362, both used for allowing the bending member 30 to be moved and bent upward or downward.

Figure 11:
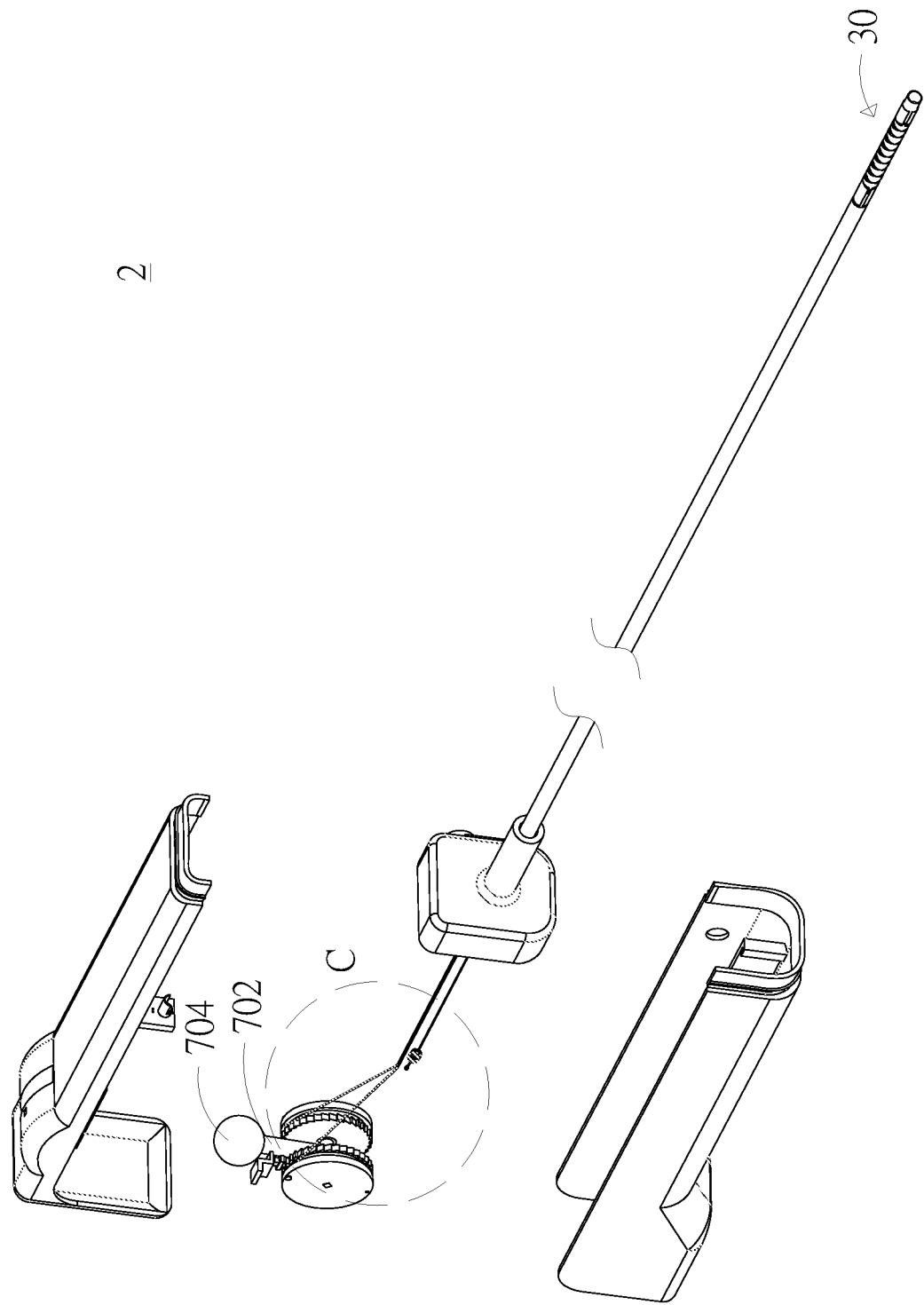
FIG. 11 is an explosive view of another embodiment according to the present invention.
Figure 12:
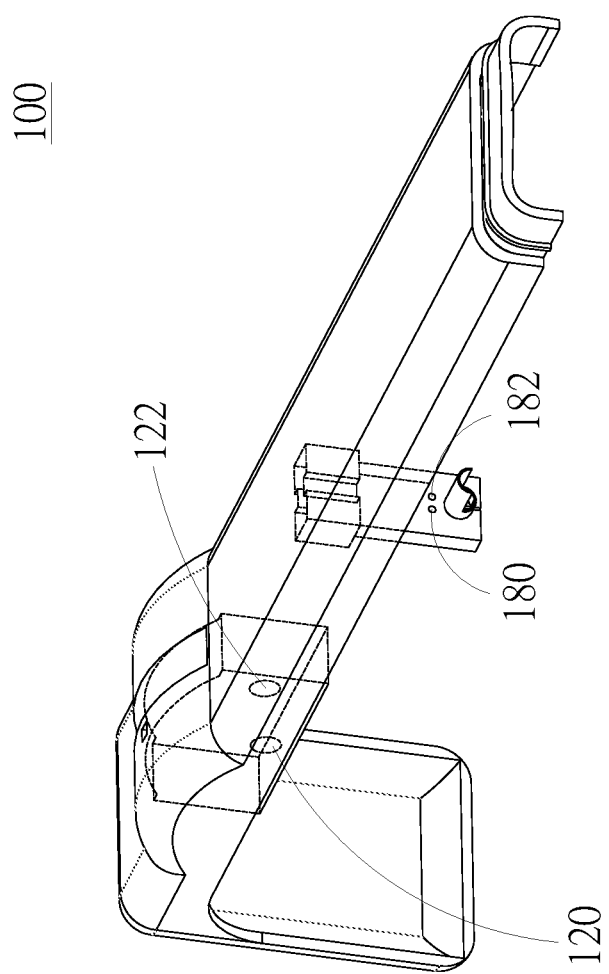
FIG. 12 is a schematic drawing showing a partial perspective view of an upper housing of an embodiment according to the present invention.
Figure 14:
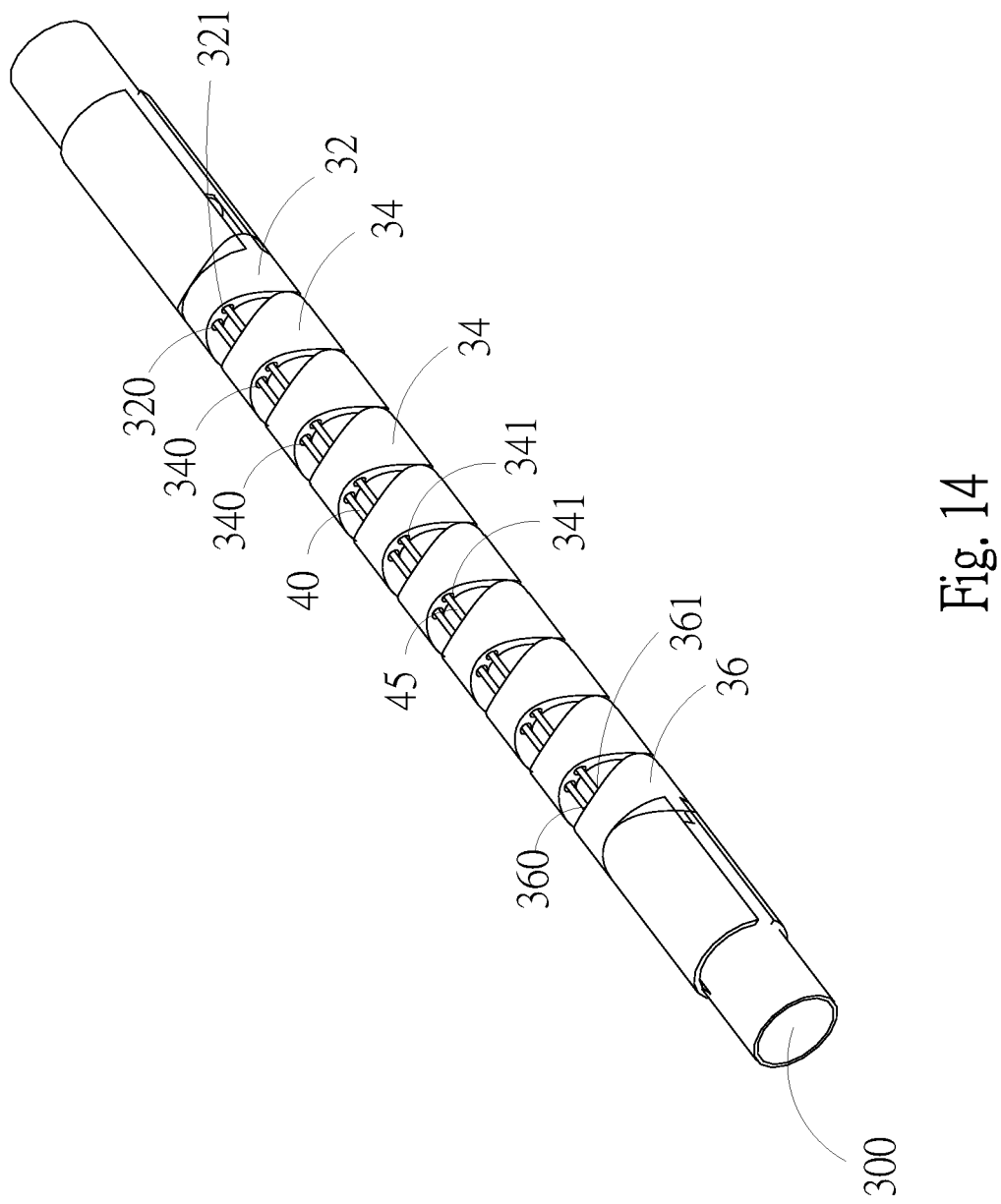
FIG. 14 is a schematic drawing showing a bending member of an embodiment according to the present invention.
Figure 15:
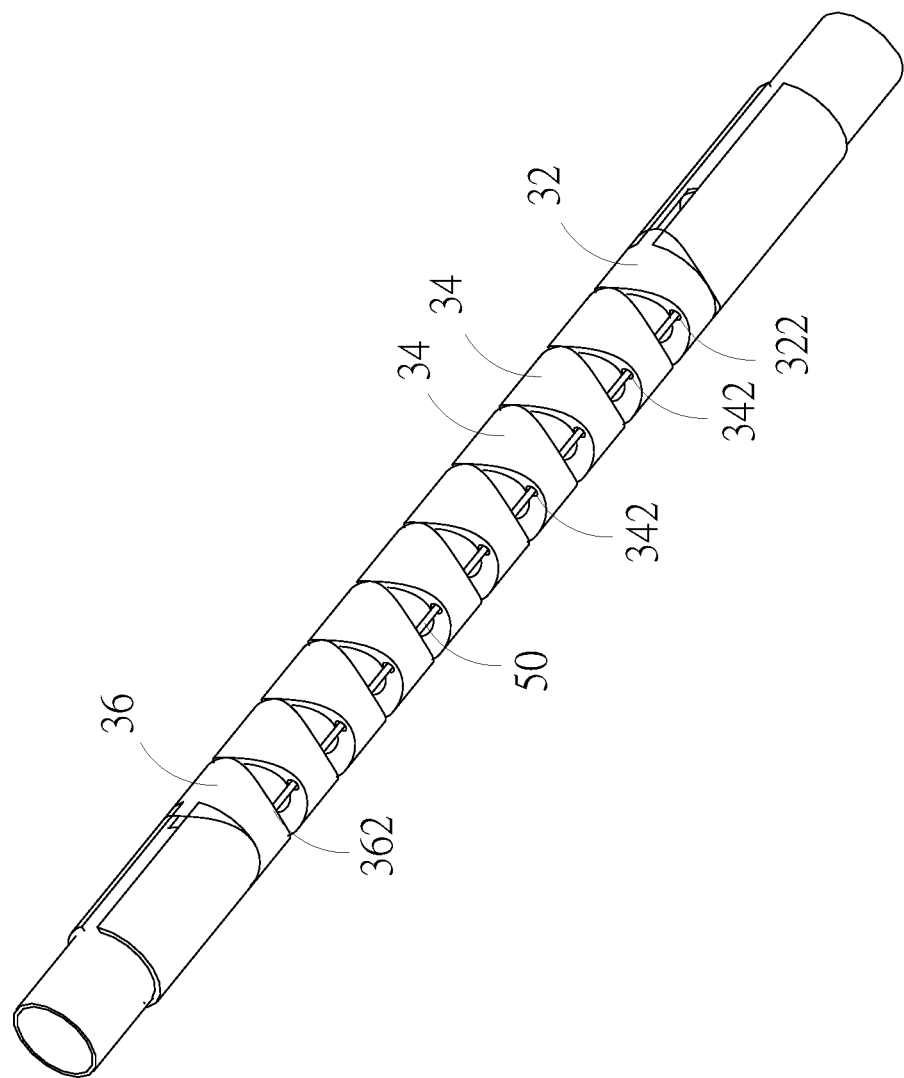
FIG. 15 is another schematic drawing showing a bending member of an embodiment according to the present invention.

Refer to Refer to FIG. 11, FIG. 12 and FIG. 13, another embodiment of an endoscope with a camera module turning function 2 according to the present invention is disclosed. As shown in the figures, the difference between this embodiment and the above one is in that the endoscope 2 of this embodiment further includes a second upper string 45 and a second roller 65. An upper tube wall of the bending member 30 is provided with a first upper turning hole (that is a collective term given to a first front upper turning hole 320, a first middle upper turning hole 340, and a first rear upper turning hole 360, as shown in FIG. 14) and a second upper turning hole (that is a collective term for a front upper turning hole 321, a middle upper turning hole 341, and a rear upper turning hole 361, as shown in FIG. 14) while a lower tube wall of the bending member 30 is provided with a lower turning hole (that is a collective term for a front lower turning hole 322, a middle lower turning hole 342, and a rear lower turning hole 362, as shown in FIG. 15). The lower turning hole 322, 342, 362 is aligned within the area between the first upper turning hole 320, 340, 360 and the second upper turning hole 321, 341, 361. The first upper string 40 is passed through the first upper turning hole 320, 340, 360 of the bending member 30 and located in the in the insertion tube 20 while the second upper string 45 is passed through the lower turning hole 322, 342, 362 of the bending member 30 and located in the in the insertion tube 20.

The first string groove 600 is formed on the circumference of the first roller 60 and one end of the first upper string 40 is connected to and mounted in the first string groove 600. Similarly, a second roller 65 is aligned with the first roller 60 and provided with a second string groove 650 on the circumference thereof. One end of the second upper string 45 is connected to and located in the second string groove 650. Two ends of the pin 700 of the control member 70 are inserted through the first insertion hole 120 and a second insertion hole 122 of the mounting slot 12 to be connected to the center of the first roller 60 and the center of the second roller 65, respectively. The first insertion hole 120 and the second insertion hole 122 are corresponding to each other. One end of the connecting rod 702 is connected to the pin 700 that is perpendicular to the connecting rod 702 and the other end of the connecting rod 702 is connected to the control button 704. By pulling the first upper string 40 and the second upper string 45, users can make the bending member 30 bend stably with less effort. Besides convenience in use, the service life of the product is also improved owing to the reduced chance of breaking strings.

Moreover, this embodiment further includes the second string 45 so that the stop member 18 of this embodiment includes not only a first stop hole 180 but also a second stop hole 185. Both the first stop hole 180 and the second stop hole 185 are aligned with the output tube 140. The first upper string 40 is passed through the first stop hole 180 and the output tube 140 to be connected to the bending member 30 while the second upper string 45 is passed through the second stop hole 185 and the output tube 140 to be connected to the bending member 30. By the first stop hole 180 and the second stop hole 185 of the stop member 18 being aligned with the center of the output tube 140, users can pull the first upper string 40 and the second upper string 45 easily to cause the bending member 30 to bend with less effort and the endoscope 2 is more convenient to use.

Refer to FIG. 14 and FIG. 15, one end of a front turning tube 32 of this embodiment is connected to the rear end of the insertion tube 20. An upper tube wall of the front turning tube 32 is provided with a first front upper turning hole 320 and a second front upper turning hole 321 while a lower tube wall of the front turning tube 32 are provided with a front lower turning hole 322. In this embodiment, a plurality of turning tubes 34 is disposed behind the front turning tube 32 in turn. An upper tube wall of each of the turning tubes 34 is provided with a first middle upper turning hole 340 and a second middle upper turning hole 341 while a lower tube wall of the respective turning tube 34 is provided with a middle lower turning hole 342. The first middle upper turning holes 340 of the turning tubes 34 are aligned and so are the second middle upper turning holes 341 and the middle lower turning holes 342. The first middle upper turning hole 340, the second middle upper turning hole 341, and the middle lower turning hole 342 of each of the turning tubes 34 are aligned with the first front upper turning hole 320, the second front upper turning hole 321, and the front lower turning hole 322 respectively. A V-shaped opening is formed between the two adjacent first middle upper turning holes 340 and an inverted V-shaped opening is formed between the two adjacent middle lower turning holes 342. A rear turning tube 36 of the embodiment is disposed behind the turning tubes 34. An upper tube wall of a first end of the rear turning tube 36 is arranged with a first rear upper turning hole 360 and a second rear upper turning hole 361 while a lower tube wall of the first end of the rear turning tube 36 is provided with a rear lower turning hole 362. The first rear upper turning hole 360, the second rear upper turning hole 361 and the rear lower turning hole 362 of the rear turning tube 36 are aligned with the first middle upper turning hole 340, the second middle upper turning hole 341 and the middle lower turning hole 342 of the turning tube 34 respectively. A camera module tube 38 is connected to the other end of the rear turning tube 36. The first upper string 40 is passed through the first front upper turning holes 320, the first middle upper turning holes 340 and the first rear upper turning hole 360 to be fixed on the rear turning tube 36 while the second upper string 45 is passed through the second front upper turning hole 321, the second middle upper turning holes 341 and the second rear upper turning hole 361 to be fixed on the rear turning tube 36. The lower string 50 is passed through the front lower turning hole 322, the middle lower turning holes 342 and the rear lower turning hole 362 to be fixed on the rear turning tube 36.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalent.

What is claimed is:

1. An endoscope with a camera module turning function comprising:
   a housing having a mounting slot that is located on an upper end thereof and provided a first insertion hole, and an output portion provided with an output tube which is hollow and located on the front end of the housing;
   an insertion tube that is hollow and having one end connected to the output portion;
   a bending member having one end thereof connected to the other end of the insertion tube, the other end thereof provided with a camera module, and two symmetrical tube walls of the bending member provided with an upper turning hole and a lower turning hole, respectively;
   a first upper string passed through the upper turning hole on one of the tube walls of the bending member and mounted in the insertion tube;
   a lower string that is arranged symmetrically to the first upper string, passed through the lower turning hole on the other tube wall of the bending member and located in the insertion tube;
   a first roller that is provided with a first string groove on the circumference thereof and one end of the first upper string is connected to the first string groove;
   a control member that is composed of a pin having one end inserted through the first insertion hole of the mounting slot and connected to the center of the first roller, a connecting rod with one end thereof perpendicular and connected to the pin, and a control button connected to the other end of the connecting rod; and
   an elastic member that includes one end thereof fixed on the housing and the other end thereof connected to the lower string; and
   a stop member fixed on the housing, the stop member is provided with a first stop hole, the first stop hole is aligned with the output tube, and the first upper string is passed through the first stop hole and the output tube to be connected to the bending member.

2. The device as claimed in claim 1, wherein the endoscope further includes a communication tube that is connected to one side of the housing.

3. The device as claimed in claim 1, wherein the stop member is provided with a fixing gap while one end of the elastic member is provided with a fixing bar and a fixing piece; one end of the fixing bar is connected to the elastic member while the other end thereof is inserted through the fixing gap and connected to the fixing piece.

4. The device as claimed in claim 1, wherein the endoscope further includes a position control member that is composed of a positioning operating part, a connecting part, an elastic part and a zigzag fixing part; one end of the connecting part is connected to the positioning operating part while the other end of the connecting part is inserted through a positioning hole of the housing and connected to the zigzag fixing part; the elastic part is inserted by the connecting part and locked between the housing and the zigzag fixing part; a plurality of saw teeth is disposed on the circumference of the inner side of the first roller while a lower part of the zigzag fixing part is jagged and able to engage with one of the saw teeth of the first roller.

5. The device as claimed in claim 1, wherein the bending member includes:
a front turning tube having one end thereof connected to a rear end of the insertion tube, a first front upper turning hole disposed on an upper tube wall thereof, and a front lower turning hole arranged at a lower tube wall thereof;
a plurality of turning tubes that is arranged behind the front turning tube in turn and each of which includes a first middle upper turning hole disposed on an upper tube wall thereof and a middle lower turning hole arranged at a lower tube; the first middle upper turning holes of the turning tubes are aligned and so are the middle lower turning holes; the first middle upper turning holes and the middle lower turning holes of the turning tubes are aligned with the front upper turning hole and the front lower turning hole respectively; a V-shaped opening is formed between the two adjacent first middle upper turning holes and an inverted V-shaped opening is formed between the two adjacent middle lower turning holes;
a rear turning tube that is disposed behind the turning tubes and composed of a first rear upper turning hole disposed on an upper tube wall of one end thereof and a rear lower turning hole arranged at a lower tube wall of the one end thereof; the first rear upper turning hole is aligned with the first middle upper turning holes of the turning tubes while the rear lower turning hole is aligned with the middle lower turning holes of the turning tubes; and
a camera module tube that is connected to the other end of the rear turning tube;
wherein the first upper string is passed through the first front upper turning hole, the first middle upper turning holes and the first rear upper turning hole to be fixed on the rear turning tube while the lower string is passed through the front lower turning hole, the middle lower turning holes and the rear lower turning hole to be fixed on the rear turning tube.

6. An endoscope with a camera module turning function comprising:
a housing having a mounting slot that is located on an upper end thereof and provided a first insertion hole and a second insertion hole, and an output portion provided with an output tube which is hollow and located on the front end of the housing;
an insertion tube that is hollow and having one end connected to the output portion;
a bending member having one end thereof connected to the other end of the insertion tube and the other end thereof provided with a camera module; an upper tube wall of the bending member being provided with a first upper turning hole and a second upper turning hole while a lower tube wall of the bending member being provided with a lower turning hole that is aligned within area between the first upper turning hole and the second upper turning hole;
a first upper string passed through the first upper turning hole of the bending member and mounted in the insertion tube;
a second upper string passed through the second upper turning hole of the bending member and mounted in the insertion tube;
a lower string passed through the lower turning hole of the bending member and located in the insertion tube;

a first roller that is provided with a first string groove on the circumference thereof and one end of the first upper string is connected to the first string groove;
a second roller that is aligned with the first roller and having a second string groove on the circumference thereof while one end of the second upper string is connected to the second string groove;
a control member that is composed of a pin having two ends thereof inserted through the first insertion hole and the second insertion hole of the mounting slot and connected to the center of the first roller and the center of the second roller respectively, a connecting rod with one end thereof perpendicular and connected to the pin, and a control button connected to the other end of the connecting rod; and
an elastic member that includes one end thereof fixed on the housing and the other end thereof connected to the lower string.

7. The device as claimed in claim 6, wherein the endoscope further includes a communication tube that is connected to one side of the housing.

8. The device as claimed in claim 6, wherein the endoscope further includes a stop member fixed on the housing and having a first stop hole and a second stop hole; the first stop hole and the second stop hole are aligned with the output tube; the first upper string is passed through the first stop hole and the output tube to be connected to the bending member while the second upper string is passed through the second stop hole and the output tube to be connected to the bending member.

9. The device as claimed in claim 8, wherein the stop member is provided with a fixing gap while one end of the elastic member is provided with a fixing bar and a fixing piece; one end of the fixing bar is connected to the elastic member while the other end thereof is inserted through the fixing gap and connected to the fixing piece.

10. The device as claimed in claim 6, wherein the endoscope further includes a position control member that is composed of a positioning operating part, a connecting part, an elastic part and a zigzag fixing part; one end of the connecting part is connected to the positioning operating part while the other end of the connecting part is inserted through a positioning hole of the housing and connected to the zigzag fixing part; the elastic part is inserted by the connecting part and locked between the housing and the zigzag fixing part; a plurality of saw teeth is disposed on the circumference of the inner side of the first roller while a lower part of the zigzag fixing part is jagged and able to engage with one of the saw teeth of the first roller.

11. The device as claimed in claim 6, wherein the bending member includes:
a front turning tube having one end thereof connected to a rear end of the insertion tube, a first front upper turning hole and a second front upper turning hole that are disposed on an upper tube wall thereof, and a front lower turning hole arranged at a lower tube wall thereof;
a plurality of turning tubes disposed behind the front turning tube in turn and each of which includes a first middle upper turning hole, a second middle upper turning hole and a middle lower turning hole; the first middle upper turning hole and the second middle upper turning hole are disposed on an upper tube wall thereof and aligned with the first front upper turning hole and the second front upper turning hole respectively; the middle lower turning hole is arranged at a lower tube wall thereof and aligned with the front lower turning hole; the first middle upper turning holes of the turning tubes are aligned and so are the second middle upper turning holes and the middle lower turning holes; a V-shaped opening is formed between the two adjacent first middle upper turning holes and an inverted V-shaped opening is formed between the two adjacent middle lower turning holes; and a rear turning tube that is disposed behind the turning tubes and composed of a first rear upper turning hole disposed on an upper tube wall of one end thereof, a second rear upper turning hole formed on the upper tube wall of the one end thereof, and a rear lower turning hole arranged at a lower tube wall of the one end thereof; the first rear upper turning hole, the second rear upper turning hole and the rear lower turning hole of the rear turning tube are aligned with the first middle upper turning holes, the second middle upper turning holes and the middle lower turning holes of the turning tubes respectively;

a camera module tube that is connected to the other end of the rear turning tube;

wherein the first upper string is passed through the first front upper turning holes, the first middle upper turning holes and the first rear upper turning hole to be fixed on the rear turning tube while the second upper string is passed through the second front upper turning hole, the second middle upper turning holes and the second rear upper turning holes to be fixed on the rear turning tube; the lower string is passed through the front lower turning hole, the middle lower turning holes and the rear lower turning hole to be fixed on the rear turning tube.

* * * * *